(12) United States Patent
Bluger

(10) Patent No.: US 6,843,870 B1
(45) Date of Patent: Jan. 18, 2005

(54) IMPLANTABLE ELECTRICAL CABLE AND METHOD OF MAKING

(75) Inventor: Henry Bluger, Victoria (CA)

(73) Assignee: Epic Biosonics Inc., Victoria (CA)

( * ) Notice: Subject to any disclaimer, the term of this patent is extended or adjusted under 35 U.S.C. 154(b) by 0 days.

(21) Appl. No.: 10/623,639

(22) Filed: Jul. 22, 2003

(51) Int. Cl.$^7$ ................................................. H01B 13/00
(52) U.S. Cl. ............................ 156/50; 156/51; 156/206
(58) Field of Search ............................ 156/47, 50, 51, 156/52, 53, 54, 55, 56, 89.12, 205, 206, 267, 268, 272.2, 272.6; 174/117 F, 117 FF, 110 AR, 110 S, 126.3, 110 FC, 98, 106 D, 102 D, 120 AR, 120 SR, 110 SR, 129 R, 133 R

(56) References Cited

U.S. PATENT DOCUMENTS

| | | | | |
|---|---|---|---|---|
| 3,540,956 A | * | 11/1970 | Arnold et al. ................ 156/54 |
| 4,000,745 A | | 1/1977 | Goldberg |
| 4,819,647 A | * | 4/1989 | Byers et al. ................ 607/116 |
| 4,945,342 A | * | 7/1990 | Steinemann ............ 174/113 R |
| 5,049,215 A | * | 9/1991 | Strauss ........................ 156/50 |
| 5,358,516 A | * | 10/1994 | Myers et al. ................ 607/116 |
| 5,468,314 A | * | 11/1995 | McGregor et al. ............ 156/56 |
| 6,265,691 B1 | * | 7/2001 | Cardineau et al. ..... 219/121.69 |
| 6,372,992 B1 | | 4/2002 | Yang |
| 6,374,141 B1 | | 4/2002 | Sass |
| 2004/0147992 A1 | * | 7/2004 | Bluger et al. ................ 607/116 |

\* cited by examiner

Primary Examiner—Gladys J P Corcoran
(74) Attorney, Agent, or Firm—Paul Smith Intellectual Property Law; Paul Smith

(57) ABSTRACT

The present invention is an implantable cable and a process to manufacture said implantable cable. The cable is composed of a biocompatible fluoropolymer, in which biocompatible conductor wires are embedded. The entire cable is heat treated at various stages to ensure the wires are securely embedded. The cable is then undulated to enhance its pliability and flexibility. Further treatment activates the outer surface of the cable, following which it may be encapsulated in silicone.

6 Claims, 9 Drawing Sheets

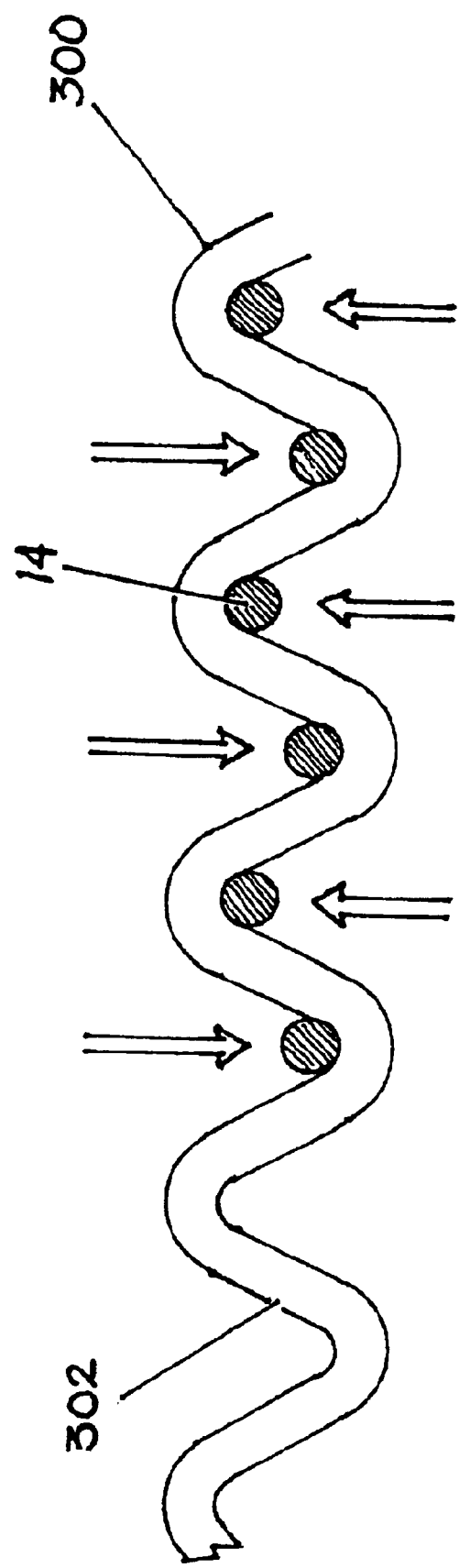

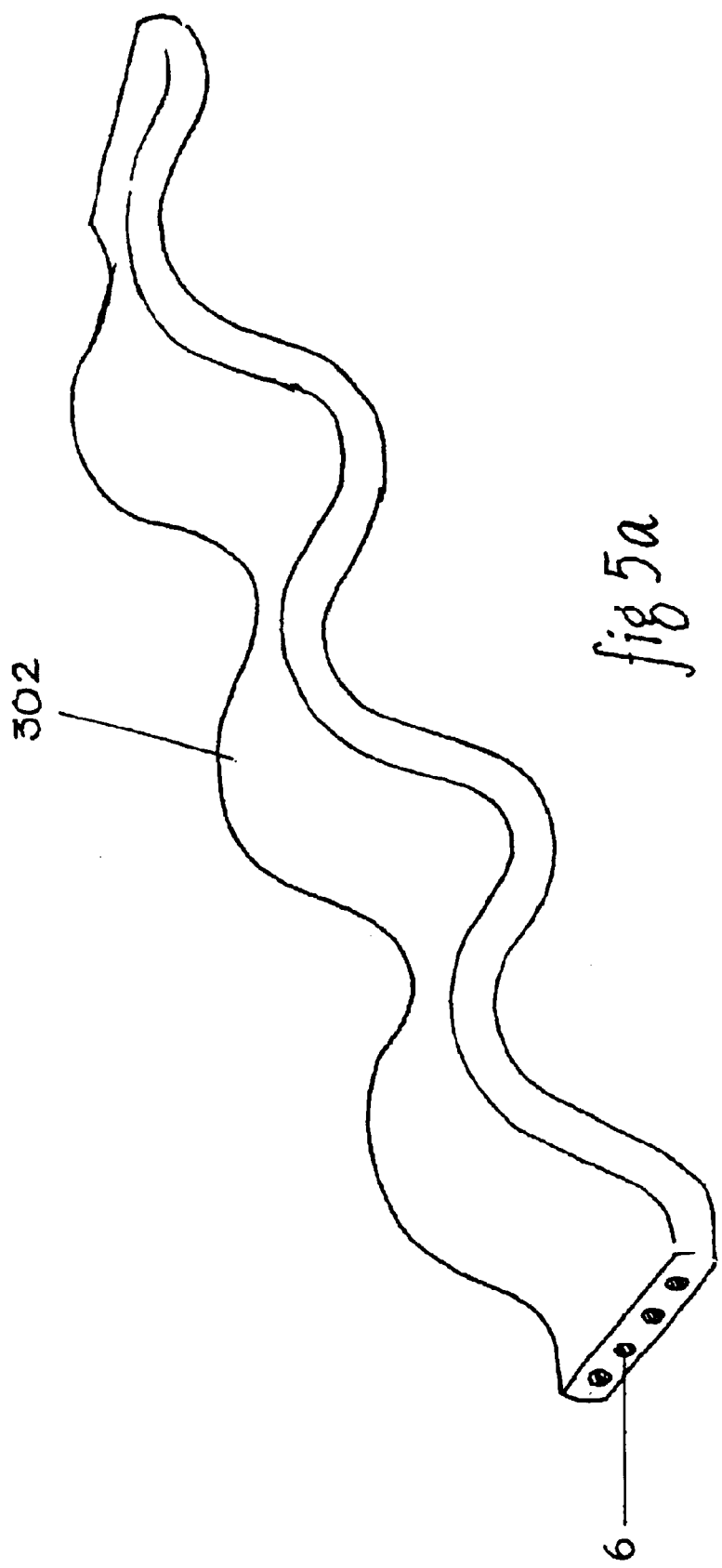

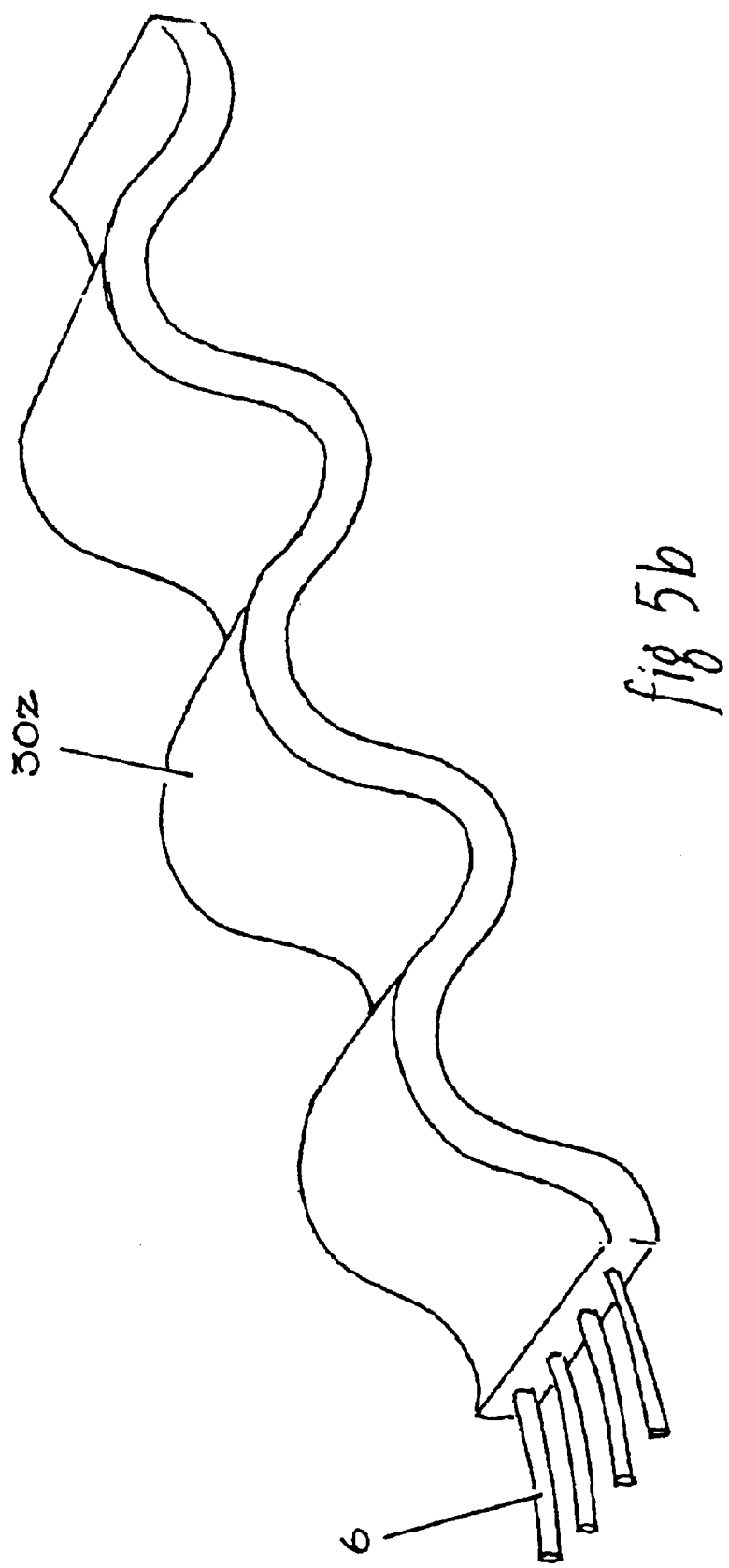

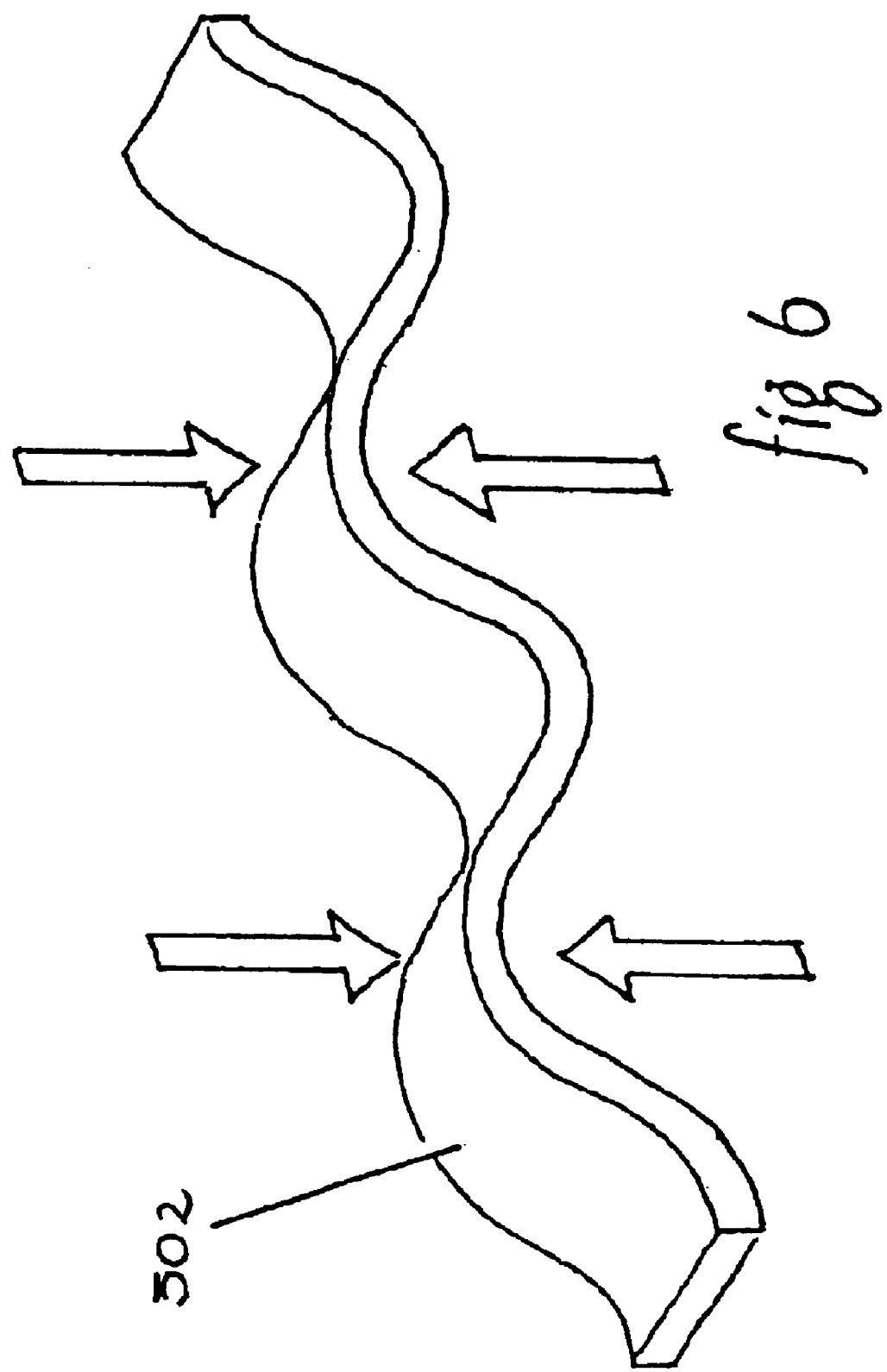

IMPLANTABLE ELECTRICAL CABLE AND METHOD OF MAKING

TECHNICAL FIELD OF THE INVENTION

This present invention relates generally to the field of implantable medical cables and conductor wires, particularly to implantable medical cable for use with various implantable electrical devices such as cochlear implants and other neurostimulation and recording applications, and to a method of fabricating such cables.

BACKGROUND OF THE INVENTION

The human body is a hostile environment to implanted medical devices and materials, particularly to chronically implanted electrical cables and leads. For example, implantable cardiac cables are typically coupled at their proximal ends with implanted pacemaker and pacemaker/cardioverter/defibrillator pulse generators. Over the years of implantation, the cables and insulation are subjected to cumulative mechanical stresses that can result in degradation of the insulation or fractures of the lead conductors with untoward effects on device performance and patient well-being.

The traditional tubular insulation is most commonly composed of an elastomeric material such as silicone or polyurethane. The combination of a helically wound conductor with elastomeric outer insulation provides conventional construction with the potential for a substantial amount of elastic deformation in the direction of the length of the lead.

An implantable electrical cable must also be completely biocompatible, in that the exterior of the cable is preferably made of biocompatible materials which are strong and flexible enough that the constant flexure caused by movement of the patient or his organs does not cause the cable to rupture. The exterior of the cable is also preferably smooth to avoid abrasion of surrounding tissue and other discomfort to the patient. The cable is also preferably compliant and supple, to avoid damage to surrounding tissue by being so stiff that it resists movement as the surrounding tissues move. A stiff and inflexible cable would apply a bias force, which would resist movement of the patient, and which would cause discomfort to the patient.

U.S. Pat. No. 4,000,745 discloses the electrical leads for cardiac stimulators comprising an insulated electrical conductive section and a lead-in securing section including a helical member which may be screwed into the heart muscle.

U.S. Pat. No. 6,374,141 discloses a bioelectrical stimulus cable in which the insulated electrical lead includes at least one fibril having a coating of rigid insulating, low friction material. A coating of shock dampening elastomeric, insulating material is tightly set about the rigid, insulating, low friction material. In one preferred embodiment, the cable includes a braided sheath encompassing a portion of the cable and increasing the tensile strength of the cable.

Notwithstanding the variety of the implantable cable designs that have been proposed, there is still a desire to improve the mechanical characteristics and the product capability of the implantable electrical cables.

An implantable cable is preferably thin. Cables that have many wires will become stiffer as the numbers of parallel conductors increases. A cable should be readily interconnectable with other devices, that is, having a grouping or arrangement of conductors that are dimensionally controlled and predictably located for reliable fastening to other devices.

It is thus an object of the present invention to provide an implantable cable which can withstand constant flexure during long term chronic implantation.

A still further object of the present invention is to provide an implantable cable which is encased with fluoropolymer such as FEP or PFA A further object of the present invention is to provide an implantable cable having improved mechanical characteristics and improved manufacturability.

A still further object of the invention is to provide a manufacturing process for an implantable cable which can be manufactured in a simple and reliable way.

These and other objects of the invention will be appreciated by reference to the summary of the invention and to the detailed description of the preferred embodiment that follow. It will be appreciated that all of the foregoing objectives may not be satisfied simultaneously by the preferred embodiment or by each of the claims.

SUMMARY OF THE INVENTION

In accordance with one aspect of the present invention, a process to manufacture an implantable cable comprises the steps of: a) establishing a number of grooves on a first fluoropolymer film layer; b) positioning biocompatible wires into said grooves; c) applying heat to confine said wires into said grooves; d) deposing a second fluoropolymer layer; e) encapsulating a resulting structure by applying heat; f) undulating a further resulting structure; g) activating the surface of the fluoropolymer film layer, and h) encapsulating a final structure with silicone.

The first and second fluoropolymer layers are preferably comprised of FEP (flurinated ethylene propylene) or PFA (perfluoralkoxy polyer). The conductor wire is preferably comprised of Pt (platinum) or Pt/Ir (platinum/iridium). The tip portion of the implantable cable may be cut away to establish lead through laser cutting. The conductor wires may have a flat, round, oval or rectangular cross section.

The foregoing was intended as a broad summary only and of only some of the aspects of the invention. It was not intended to define the limits or requirements of the invention. Other aspects of the invention will be appreciated by reference to the detailed description of the preferred embodiment and to the claims.

BRIEF DESCRIPTION OF THE DRAWINGS

FIG. 4B shows another method of undulating an implantable cable according to the present invention.

FIG. 5A is a perspective view of an undulated implantable cable according to the present invention.

FIG. 5B is perspective view of an undulated implantable cable with the fluoropolymer material removed from the tip.

FIG. 6 is a sectional view of an undulated implantable cable undergoing plasma treatment.

DETAILED DESCRIPTION OF THE PREFERRED EMBODIMENT

The following describes the best mode presently contemplated for carrying out the invention. This description is not to be taken in a limiting sense, but is made merely for describing the general principles of the invention. The scope of the invention should be determined with reference to the claims.

Figure 1A:
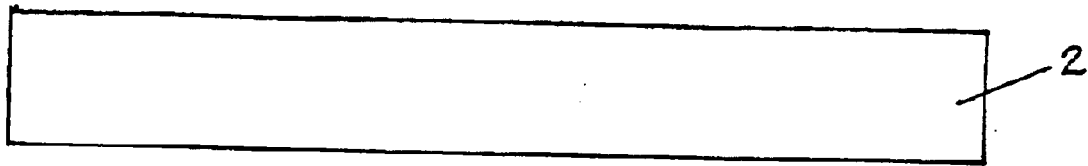
FIG. 1A is a sectional view of a fluoropolymer film used to manufacture an implantable cable according to the present invention.

FIG. 1A is a sectional view of a fluoropolymer film 2 used to manufacture an implantable cable according to the present invention. FEP or PFA film 2 is used in the preferred embodiment of the present invention. However, it is possible to use other melt processable biomaterials such as fluorocarbons PVDF, PCTFE, ECTFE, ETFE, MFA (a copolymer of TFE and PVE), polyethylene's and polypropylenes. The thickness of the film 2 is preferably about 20–100 µm.

Figure 1B:
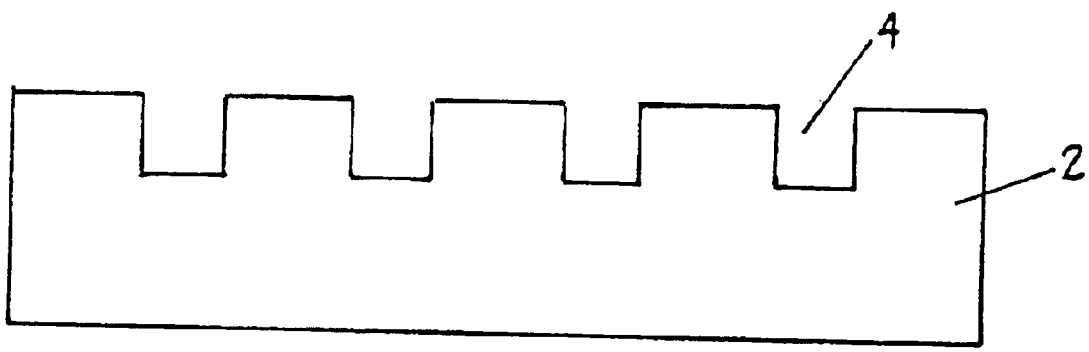
FIG. 1B is a sectional view of a fluoropolymer film having grooves to manufacture an implantable cable according to the present invention.

FIG. 1B is a sectional view of a fluoropolymer film 2 having grooves 4 to manufacture an implantable cable according to the present invention. A plurality of grooves 4 are established within the FEP film 2 through laser cutting or other method such as thermal forming and sawing.

Figure 2A:
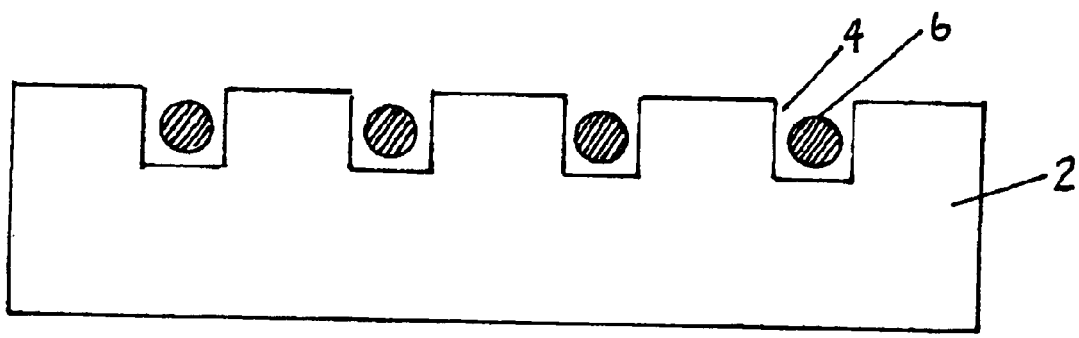
FIG. 2A is a sectional view of a fluoropolymer film within which a conductor wire is placed in each groove.

Grooves 4 may be used to locate the conductor wires used to deliver electrical signals. FIG. 2A is a sectional view of a fluoropolymer film as in FIG. 1B with a conductor wire 6 placed in each groove 4 in the FEP film 2. Conductor wire 6 may be made of Pt or a Pt/Ir alloy. The conductor wires 6 may preferably have round, oval or rectangular cross sections. Instead of Pt or Pt/Ir, well known to those skilled in the art, titanium (and some alloys thereof), platinum, tantalum, or gold may be used.

Figure 2B:
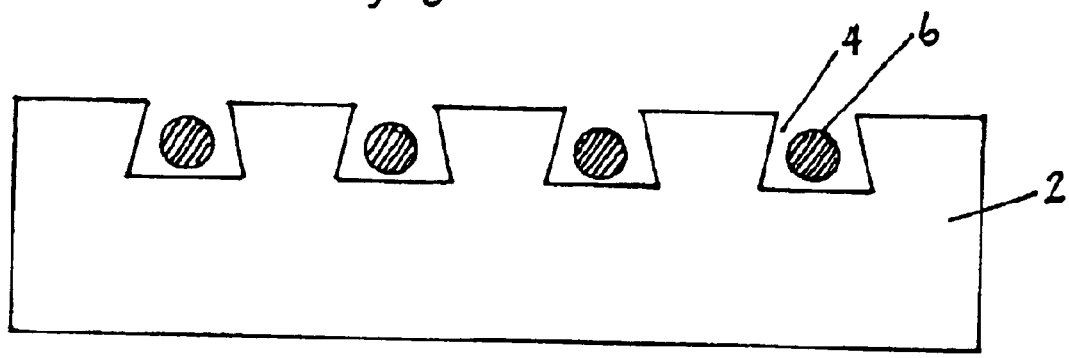
FIG. 2B is a sectional view of a fluoropolymer film having conductor wires after a thermal treatment.

FIG. 2B is a sectional view of a fluoropolymer film as in FIG. 2A after a thermal treatment. After locating wires 6 into grooves 4 shaped on film 2, heat and pressure are applied to overall structure to confine the wires within the film 2. This thermal treatment ensures the wire conductors 6 are retained within the film 2. Usually, in the case of FEP film, a thermal treatment at 240–350 QC is applied to the structure.

Figure 3A:
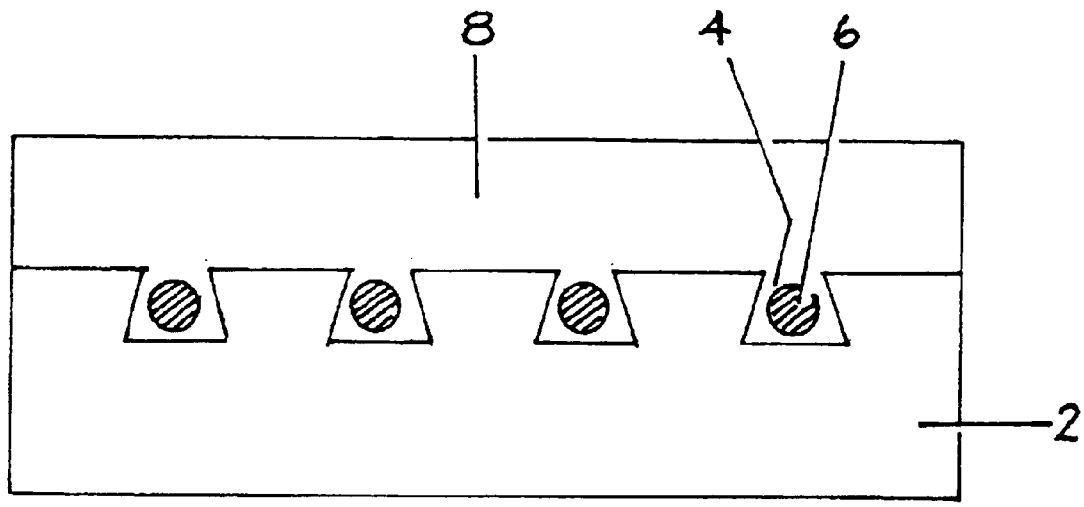
FIG. 3A is a sectional view of a fluoropolymer film having conductor wires on which another fluoropolymer film is deposited.

FIG. 3A is a sectional view of a fluoropolymer film as in FIG. 2B on which another fluoropolymer film 8 is deposited. To further encapsulate the wires 6, and to ensure the wires 6 will be held tightly within the structure, another film 8 is deposited on the film 2 in which the conductor wires are located. Film 8 is preferably FEP, but, as with film 2, may be PFA or other melt processable biomaterials such as fluorocarbons PVDF, PCTFE, ECTFE, ETFE, MFA (a copolymer of TFE and PVE), polyethylenes and polypropylenes.

Figure 3B:
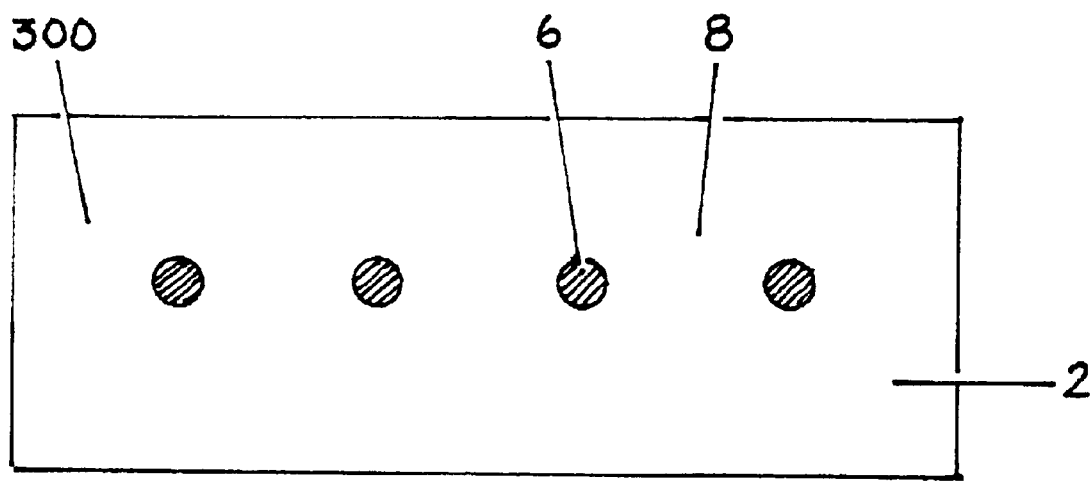
FIG. 3B is a sectional view of the final structure of an implantable cable according to the present invention.

FIG. 3B is a sectional view of the final structure of an implantable cable according to the present invention. After depositing film 8, another thermal treatment is applied, forming a relatively flat implantable cable 300. The conductor wires 6 are thus tightly encapsulated within the fluoropolymer film forming implantable cable 300.

Figure 4A:
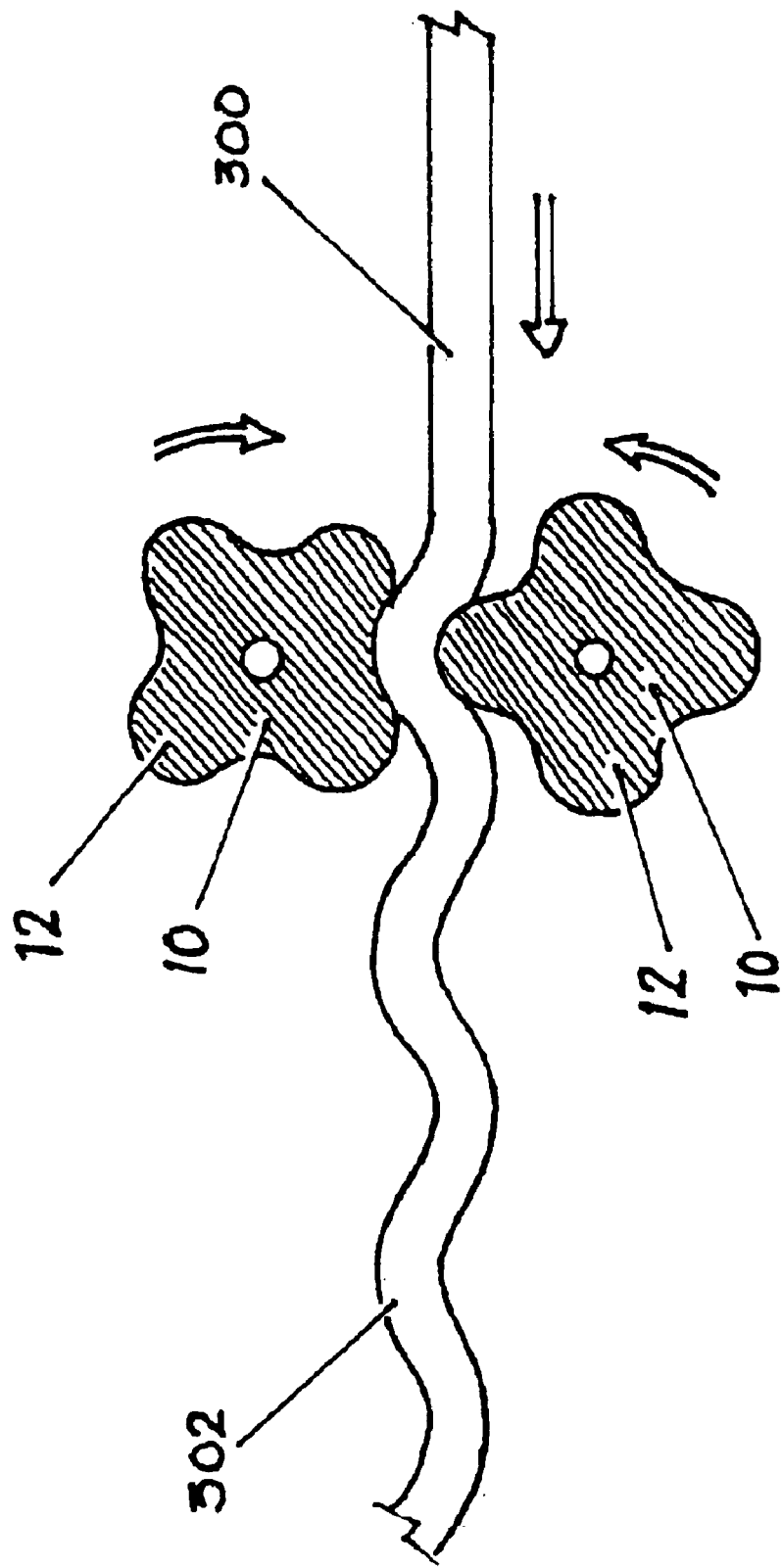
FIG. 4A shows one method of undulating an implantable cable according to the present invention.

To increase cable flexibility and pliability, by allowing ready expansion or contraction of the cable, it is preferred that the cable 300 be undulated. FIGS. 4A and 4B show possible methods of undulating an implantable cable 300 according to the present invention. As shown in FIG. 4A, two opposing drums 10 may be used. The drums 10 preferably have fine teeth 12 or other meshing projections which roll over the surface of implantable cable 300, thereby undulating the implantable cable 300 and forming undulated cable 302. The drums 10 revolve at a certain speed and press the implantable cable 300 from both sides. This is a very efficient method of manufacturing undulated cable 302.

FIG. 4B shows an alternative method of undulating an implantable cable 300 according to the present invention. There are provided a number of pins 14, which revolve at a certain speed. The pins 14 are positioned in a zigzag formation. Then, the implantable cable 300 is undulated, forming undulated cable 302, by feeding it through the pins 14. The undulation process preferably takes place at an elevated temperature.

FIG. 5A is a perspective view of an undulated implantable cable 302 according to the present invention. As shown in FIG. 5B, the film on the tip of the undulated implantable cable 302 is then partly cut away to expose the conductor wires 6. While any suitable method to strip the cable tip without damaging the wires may be used, laser cutting is the preferred method. The exposed wires may then be welded to either a connector or an exposed junction, in order to connect undulated implantable cable 302 to another device.

The undulated implantable cable 302 needs additional plasma treatment or sodium treatment to be activated. FIG. 6 is a sectional view of an undulated implantable cable 302 undergoing a plasma treatment. The cable is treated on both sides, as shown by the arrows. This treatment facilitates the adhesion of an encapsulating layer of silicone to the implantable cable 302.

Figure 7A:
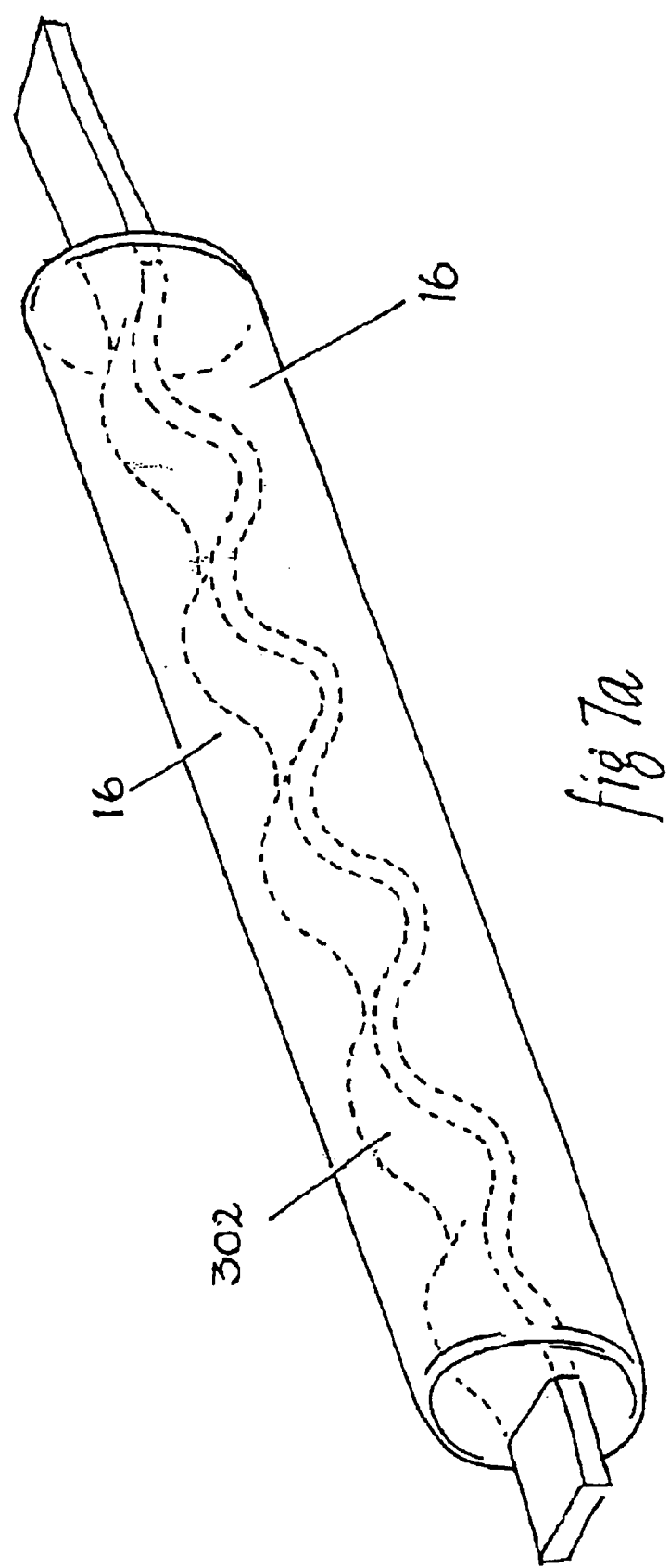
FIG. 7A shows an undulated implantable cable encapsulated with silicone.
Figure 7B:
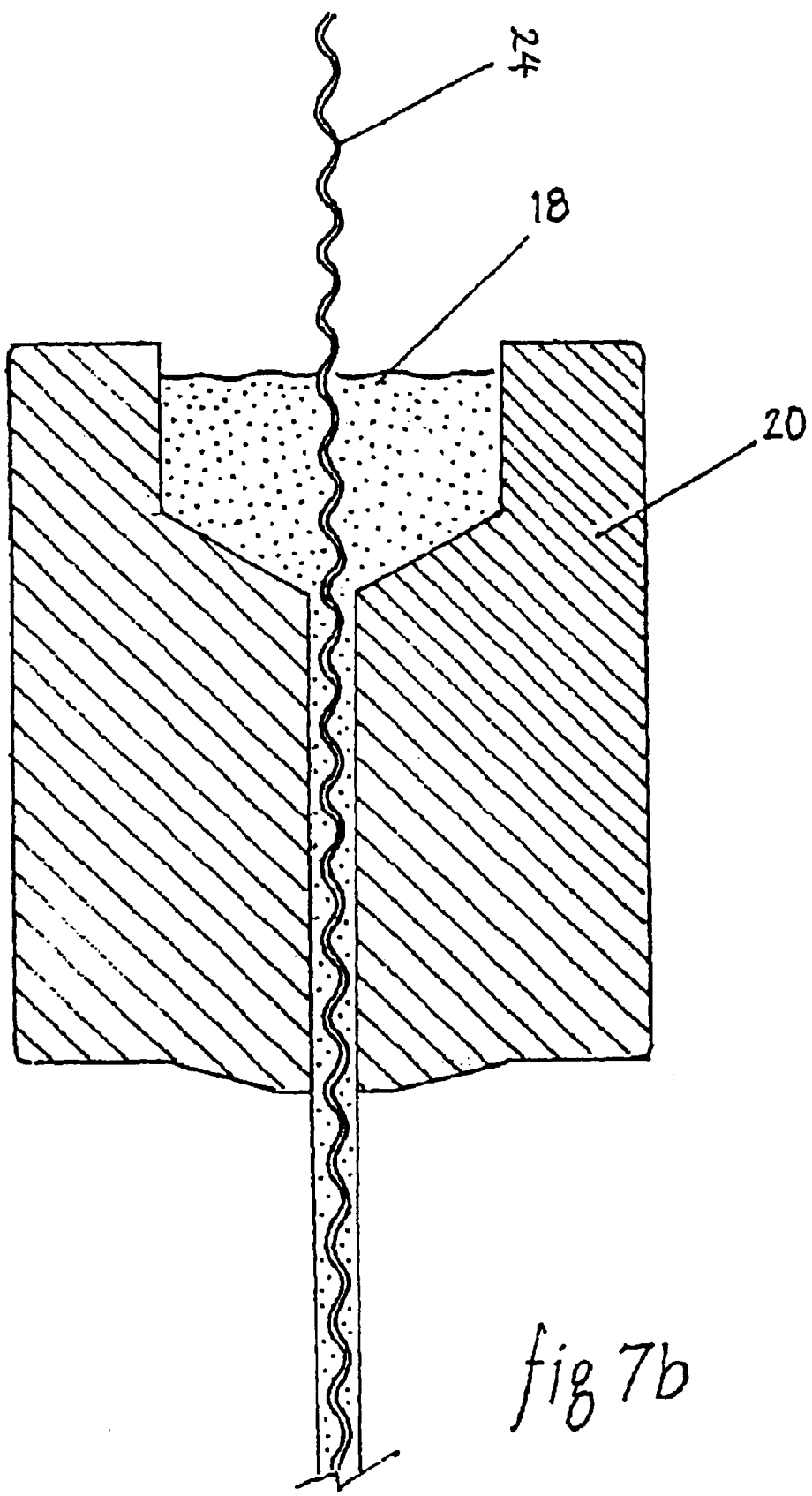
FIG. 7B shows a method of encapsulating an undulated implantable cable with silicone.

After undulating the cable, it is preferred to encapsulate the implantable cable 302 with silicone. Silicone is preferred as it is highly elastic and is therefore capable of being elongated with an elastic recovery to its initial shape. FIG. 7A shows an undulated implantable cable 302 encased with a silicone coating 16 by an injection molding method. FIG. 7B shows another method in which the undulated implantable cable 302 is fed through a bottle shaped tool 20 through which liquid silicone 18 is flowing, thereby encapsulating the undulated implantable cable 302. A heat coil or some other heat source (not shown) may be used to provide heat to keep the silicone 18 warn and flowable, to ensure good uniform contact and coverage over all sides of the undulated implantable cable 302.

It will be understood that in general these implantable medical cables have extremely wide application in the medical device field.

Moreover, as described above, it is seen that the implantable cable described herein may be manufactured using low cost technology and simple-to-implement manufacturing techniques for mass production.

Finally, it is seen that the implantable cable of the present invention may be safely and reliably used in various medical devices.

The above descriptions are intended to illustrate the preferred and alternative embodiments of the invention. For example, the process for stripping out the undulated cable can be done in the last stage after encasing the cable with silicone. It will be appreciated that modifications and adaptations to such embodiments may be practiced without departing from the scope of the invention, such scope being most properly defined by reference to this specification as a whole and to the following claims.

I claim:

1. A process to manufacture an implantable cable, said process comprising the steps of:
   establishing a plurality of grooves on a first fluoropolymer film layer;
   positioning biocompatible conductor wires into one or more of said grooves;
   applying heat to confine said wires into said grooves;
   depositing a second fluoropolymer layer on said first fluoropolymer film layer with said confined wires to form a first structure;
   creating a second structure with outer surfaces by encapsulating said confined wires with said first and second fluoropolymer layers in said first structure through application of heat;
   undulating said second structure;
   activating said outer surfaces of the said second structure to form a final structure; and
   encapsulating said final structure with silicone to form said implantable cable.

2. The process of claim 1, wherein said first and second fluoropolymer film layers are comprised of FEP or PFA.

3. The process of claim 1, wherein said conductor wires are comprised of Pt or Pt/Ir.

4. The process of claim 1, wherein the first and second fluoropolymer layers are removed from an end portion of said implantable cable to partially expose one or more conductor wires.

5. The process of claim 4, wherein said removed first and second fluoropolymer layers from said end portion are removed through laser cutting.

6. The process of claim 3, wherein said conductor wires have round, oval or rectangular cross sections.

* * * * *